(12) United States Patent
Reiber et al.

(10) Patent No.: US 11,741,602 B2
(45) Date of Patent: *Aug. 29, 2023

(54) HEARTBEAT BASED SELECTION OF IMAGES FOR CARDIOVASCULAR MODEL

(71) Applicant: Medis Associated B.V., Leiden (NL)

(72) Inventors: Johan Hendrikus Christiaan Reiber, Rotterdam (NL); Gerhard Koning, Voorschoten (NL); Johannes Petrus Janssen, Leiderdorp (NL); Yingguang Li, Shanghai (CN)

(73) Assignee: Medis Associated B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,247

(22) Filed: Nov. 30, 2021

(65) Prior Publication Data

US 2022/0092778 A1    Mar. 24, 2022

Related U.S. Application Data

(63) Continuation of application No. 16/700,688, filed on Dec. 2, 2019, now Pat. No. 11,216,944.

(30) Foreign Application Priority Data

Nov. 30, 2018    (NL) .................................. 2022109

(51) Int. Cl.
  *G06T 7/00*    (2017.01)
  *G06T 19/00*   (2011.01)
  (Continued)

(52) U.S. Cl.
  CPC ........ *G06T 7/0012* (2013.01); *A61B 5/02416* (2013.01); *A61B 5/349* (2021.01);
  (Continued)

(58) Field of Classification Search
  CPC ..... G06T 7/0012; G06T 11/003; G06T 17/00; G06T 19/00; G06T 2200/04;
  (Continued)

(56) References Cited

U.S. PATENT DOCUMENTS

2008/0281218 A1    11/2008  Lei et al.
2015/0268039 A1     9/2015  Tu et al.
(Continued)

FOREIGN PATENT DOCUMENTS

EP    3210537 A1    8/2017
WO    2017200381 A1   11/2017

OTHER PUBLICATIONS

Jeff Smit et al. May 15, 2019 Comparision of Diagnostic Performance of Quantitative Flow Ratio in Patients with Versus Without Diabetes Mellitus. The American Journal of Cardiology. vol. 123. Issue 10. pp. 1722-1728.

(Continued)

*Primary Examiner* — Siamak Harandi
(74) *Attorney, Agent, or Firm* — Banner & Witcoff, Ltd.

(57) ABSTRACT

To create a 3D model of part of a cardiovascular system, two 2D images taken of different orientations of the cardiovascular system may be combined. The 2D images originate from video streams taken at different points in time, which comprise frames showing a beating heart, and thus a moving cardiovascular system. Because of this movement, not just any random set of two 2D images may result in useable 3D model. To select a proper set of two 2D images, a method is provided wherein said selection is based on cardiac cycle data. The cardiac cycle data may comprise heart activity data as a function of time and timing data on cycle events. These cycle events may be repetitive, as the same events occur with every heartbeat. The selected frames are preferably selected at, or approximately at, similar events.

20 Claims, 3 Drawing Sheets

(51) Int. Cl.
  *A61B 5/024* (2006.01)
  *G06T 11/00* (2006.01)
  *G06T 17/00* (2006.01)
  *A61B 5/349* (2021.01)

(52) U.S. Cl.
  CPC ............ *G06T 11/003* (2013.01); *G06T 17/00* (2013.01); *G06T 19/00* (2013.01); *G06T 2200/04* (2013.01); *G06T 2207/30048* (2013.01); *G06T 2210/41* (2013.01)

(58) Field of Classification Search
  CPC ....... G06T 2207/30048; G06T 2210/41; A61B 5/349; A61B 5/02416; A61B 5/7292; A61B 5/107; G16H 30/40
  See application file for complete search history.

(56) References Cited

U.S. PATENT DOCUMENTS

| | | | |
|---|---|---|---|
| 2017/0065230 A1 | 3/2017 | Sinha et al. |
| 2017/0172510 A1 | 6/2017 | Homyk et al. |
| 2017/0347985 A1 | 12/2017 | Redel et al. |

OTHER PUBLICATIONS

Shengxian Tu et al. Jan. 20, 2012. In vivo comparison of arterial lumen dimensions assessed by co-registered three-dimensional (3D) quantitative coronary angiography, intravascular ultrasound and optical coherence tomography. The International Journal of Cardiovascular Imaging. vol. 28. Issue 6. pp. 1315-1327.

S-hengxian Tu et al. Jul. 2014 Fractional Flow Reserve Calculation From 3-Dimensional Quantitative Coronary Angiography and TIMI Frame Count. JACC Cardiovascular Interventions. vol. 7. Issue 7. pp. 768-777.

Aug. 29, 2019, Dutch Search Report, NL 2022109.

Shengxian Tu et al., "Assessment of obstruction length and optimal viewing angle from biplane X-ray angiograms", Sep. 18, 2009, The International Journal of Cardiac Imaging, vol. 26, No. 1, pp. 5-17.

Lili Liu et al., "The impact of image resolution on computation of fractional flow reserve: coronary computed tomography angiography versus 3-dimensional quantitative coronary angiography", Oct. 27, 2015, International Journal of Cardiovascular Imaging, vol. 32, No. 3, pp. 513-523.

Miao Chu et al., "Quantification of disturbed coronary flow by disturbed vorticity index and relation with fractional flow reserve", Jun. 1, 2018, Atherosclerosis, vol. 273, pp. 136-144.

HEARTBEAT BASED SELECTION OF IMAGES FOR CARDIOVASCULAR MODEL

CROSS-REFERENCE TO RELATED APPLICATIONS

This application is a continuation of U.S. application Ser. No. 16/700,688 filed Dec. 2, 2019, which claims priority to Dutch patent application NL 2022109, filed Nov. 30, 2018. Benefit of the filing date of each of these prior applications is hereby claimed. Each of these prior applications is hereby incorporated by reference in its entirety.

FIELD OF THE INVENTION

The invention relates to a device for and method of building a 3D model of part of a cardiovascular system.

BACKGROUND 3D models of the cardiovascular system are used in different applications, for example by medical professionals. To create a 3D model, a minimum of two 2D images need to be combined, wherein the two 2D images comprise image data of different views of the cardiovascular system. The two 2D images are often made by the same imaging device, which has to be reoriented between capturing the first and the second 2D image for obtaining the two different views of the cardiovascular system. Because of the reorientation, the two 2D images are disjoint in time. A manual selection of the 2D images has to be made to find a compatible set of 2D images for creating the 3D model.

SUMMARY

It is preferred to provide a method for automatically building a 3D model of at least a part of a cardiovascular system.

A first aspect provides a method of building a 3D model of at least a part of a cardiovascular system, comprising receiving a first video stream comprising first frames comprising image data on a cardiovascular system over a first period of time, receiving a second video stream comprising second frames comprising image data on the cardiovascular system over a second period of time, wherein the first period of time is in disjunction from the second period of time, obtaining cardiac cycle data related to the cardiovascular system from the first period of time and the second period of time, selecting one of the first frames and one of the second frames based on the cardiac cycle data, and building the 3D model of part of the cardiovascular system using the selected frames.

The first video stream and the second video stream may have been captured by a medical imaging device such as an X-ray imaging device, CT-scanner, MR-scanner, or using intravascular imaging devices, such as IntraVascular Ultra-Sound (IVUS) or Optical Coherence Tomography (OCT), or using any other imaging technique on any other medical imaging device.

The video streams comprise a plurality of consecutive frames of a certain period of time, which may for example be in the order of seconds or minutes. The first period of time being in disjunction from the second period of time here means that the first period of time does not overlap with the second period of time. Hence, a time gap is present between the first period of time and the second period of time. The time gap may comprise any amount of time, for example in the order of several minutes.

Image data may be represented as one or more matrices of pixels which correspond to an image obtained by the imaging device. The matrix may comprise any amount of pixels, and the pixels may represent a certain colour, intensity, grayscale value, or any other value.

During the first period of time, the first frames comprising image data on the cardiovascular system over the first period of time have been obtained by the imaging device. During the second period of time, the second frames comprising image data on the cardiovascular system over the period of time have been obtained by an imaging device, which preferably is the same imaging device as used in the first period of time to prevent the need of a second imaging device—yet, use of two imaging devices that capture image data simultaneously, during overlapping periods or non-overlapping periods in time is not excluded. The imaging device and the cardiovascular system have to be reoriented relative to each other in order to obtain 2D images from different orientations to create the 3D model. This reorientation may be performed in the time gap between the first period of time and the second period of time.

The image data on the cardiovascular data may comprise image data on arteries which may be at least partially filled with a contrast dye based on for example iodine or any other suitable material known and/or available. The contrast dye may increase visibility of the arteries in the image data.

As the video streams comprise consecutive frames captured over a certain time window during which the heart of the patient, human or animal, has been beating, the cardiovascular system may be depicted in various orientations and/or various positions in different frames. Picking a random frame from the first video stream and a random frame from the second video stream may very likely result in a non-optimal 3D model.

Whereas in the state of the art the selection of one of the first frames and one of the second frames is done manually, i.e. based solely on user input, according to the first aspect this is now done based on the obtained cardiac cycle data. Using this cardiac cycle data, two frames may be found which show the cardiovascular system in a similar state within the cardiac cycle. The cardiac cycle data comprises data on the states of the heart between the beginning of a heartbeat up until the beginning of the next heartbeat, and thus the diastole and systole periods and starts and ends thereof, for one or more heartbeats or parts of heartbeats.

Having an automatic method for selecting images for creating the 3D model may decrease working time and errors by a medical professional which may in turn decrease costs of creating the 3D model. Also, the quality of the 3D model may increase when an optimal set of frames is found within the first video stream and the second video stream. Selected images may be provided to a user for confirmation prior to creation of the 3D model.

The cardiac cycle data may thus comprise heart activity data as a function of time. With heart activity, any data related to the cardiovascular system should be understood, including for example ventricular activity data and/or atrial activity data.

The cardiac cycle data may comprise timing data on a first cycle event within the first period of time and timing data on a second cycle event within the second period of time. In such a case, the selection of the one of the first frames may be based on the timing data of the first cycle event and the selection of the one of the second frames may be based on the timing data of the second cycle event. The second cycle event may be equivalent to the first cycle event.

The timing data may comprise an absolute time, such as 2.02 AM or 5.17 PM, optionally on a specific data in a specific time-zone, or a relative time from a starting time, for example 0 minutes 2 seconds, or 10 minutes 25 seconds. The timing data may also be linked to a frame, considering that the video streams comprise frames at a known certain framerate, such as 30 or 60 frames per second. The starting time of capturing a video stream and the starting time of capturing cardiac cycle data may be linked, for example by a common trigger, such that the timing data of the cardia cycle data may be easily correlated to the frames of the video stream.

The cardiac cycle data may thus comprise a plurality of data points, wherein each data point is related to a certain point in time comprised by the timing data. Interpolation between discrete points in time of the timing data may be applied to obtain an interpolated data point at a point in time between two discrete points in time.

The first cycle event and the second cycle event may correspond to the end of diastole. At this event, movement of the cardiovascular system may be the least in the heart cycle, which may be advantageous for the quality of the image data of the first frames and the second frames. A higher quality of these frames may result in a higher quality 3D model. A higher quality may relate to a higher contrast, sharpness, any other image quality parameter or a combination thereof.

An embodiment of the first aspect comprises selecting, from the first frame, based on the first cycle event, multiple first selected frames related to the events and selecting, from the second frames, based on the second cycle event, multiple second selected frames related to the event. In at least a first of the first selected frames and the second selected frames, an image region is identified depicting a cardiovascular structure. In at least two frames of the first of the first selected frames and the second selected frames, values of at least one characteristic of the identified image region are compared and based on the comparing, from the selected first of the first selected frames and the second selected frames, a first model frame is selected. The 3D model is built using the first model frame. This example provides for automatic selection of a particular frame from a set of frames related to a particular event in the cardiac cycle data.

Another embodiment comprises determining, in at least a first of the first selected frames and the second selected frames, a length of the cardiovascular structure wherein the at least one characteristic is the determined length. For proper assessment of any stenotic regions in the vessel and effects thereof, it is preferred to assess a long as possible section of the vessel under scrutiny.

A further embodiment comprises determining, within an image region comprising the identified cardiovascular structure, in at least a first of the first selected frames and the second selected frames, a brightness level of at least one of the image regions or sub-regions thereof, wherein the at least one characteristic is the determined brightness. For detection of stenotic areas, a high contrast between the inner volume of the vessel and the surrounding tissue is preferred.

In again another embodiment, the comparing is applied to least two selected frames subsequent in time. As the contrast fluid travels through the vessel under scrutiny, the contrast fluid dilutes in the blood—in particular when no further contrast fluid is introduced. By comparing brightness and/or length of the vessel filled with contrast fluid, increase or decrease of the length and/or dilution may be determined. Based on that determination or those determinations, a model frame may be selected.

In yet a further embodiment, the first model frame is selected as the frame having the longest length and of which the brightness in the identified image region or a sub-region thereof is lower than of the identified image region or a sub-region thereof in a subsequent frame. This embodiment provides for selection of a model frame that is the longest, without dilution at the start of the vessel or outlet of the contrast fluid injecting catheter.

In examples of the method, the first cycle event and the second cycle event correspond to other events such as ventricular diastole, atrial systole, ventricular systole, atrial diastole, the start of ending of an event, or any other identifiable heart event.

When electrocardiographic (ECG) data of the first period of time and the second period of time is received, at least part of the cardiac cycle data may be obtained from this electrocardiographic data. Such electrocardiographic data may comprise a recording of electrical activity, for example expressed as a voltage, of the cardiovascular system and more specifically of the heart motion over the first period of time and the second period of time.

From the electrocardiography data the different states of the heart corresponding to cycle events during the cardiac cycle may be identified, as will be appreciated by a person skilled in the art.

When photoplethysmography data of the first period of time and the second period of time is received, at least part of the cardiac cycle data may be obtained from the photoplethysmography data. Such photoplethysmography data may have been obtained by a pulse oximeter, which may for example have been placed on a body part of the patient during the first period of time and the second period of time, for example on a fingertip, earlobe, forehead or foot.

From the photoplethysmography data the different states of the heart corresponding to cycle events during the cardiac cycle may be identified, as will be appreciated by a person skilled in the art.

Preferably, the image data comprised by the first video stream and the second video stream is obtained by a single medical imaging device. This prevents the need for a second medical imaging device, and the image data of the first video stream and the second video stream may be more compatible for building the 3D model out of when obtained by the same medical imaging device.

The cardiac cycle data in the first period of time may be obtained from the first video stream and the cardiac cycle data in the second period of time may be obtained from the second video stream.

Obtaining cardiac cycle data from a video stream may for example be based on varying distances between main arteries and branches and distances between branch points or angulations between branches, which are visible in the image data. For example, minima and maxima of these distances may indicate certain events in the cardiac cycle.

When the cardiac cycle data is obtained from the video streams, the method advantageously requires only the receiving of the first video stream and the second video stream and no additional data. Furthermore, when the cardiac cycle data is obtained from the video streams, it may be simpler to correlate the timing data of cycle events to particular frames in the video streams which may be selected for building the 3D model.

The method according to any of the examples may be carried out by a computer for building a 3D model of at least part of a cardiovascular system of a human or animal from selected frames of the first video stream and the second video stream.

A second aspect provides a data processing system comprising means for carrying out the method of building a 3D model of at least a part of a cardiovascular system according to any of the examples of this description.

A third aspect provides a computer program product comprising instructions which, when the program is executed by a computer, cause the computer to carry out any of the examples of the method of building a 3D model of at least a part of a cardiovascular system.

A fourth aspect provides a computer-readable storage medium comprising instructions which, when executed by a computer, cause the computer to carry out any of the examples of the method of building a 3D model of at least a part of a cardiovascular system.

BRIEF DESCRIPTION OF THE DRAWINGS

The various aspects and examples will now be discussed in conjunction with figures. In the figures.

DETAILED DESCRIPTION

Figure 1A:
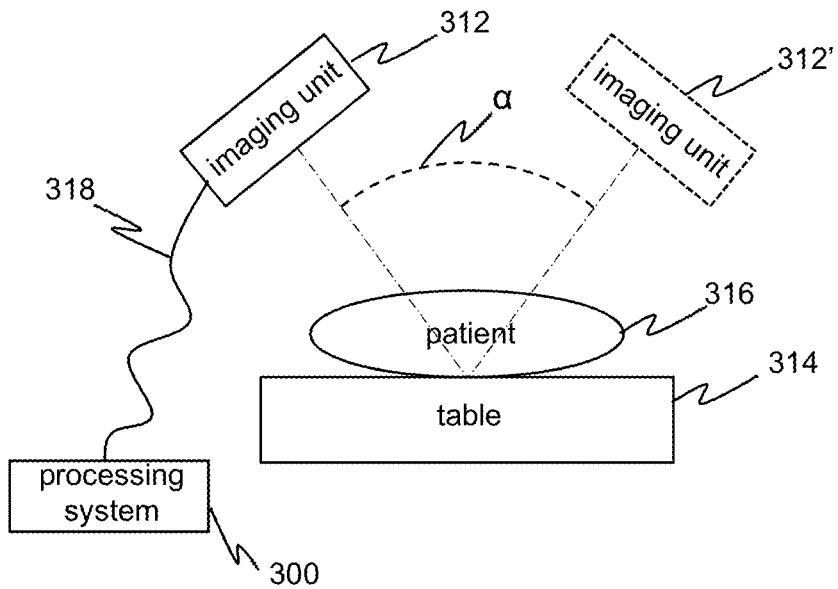
FIG. 1A shows a schematic view of a medical imaging device.

FIG. 1A shows a schematic view of a medical imaging device 310, comprising an imaging unit 312 shown in a first position and in a second position, wherein the imaging unit in the second position has reference numeral 312'. The medical imaging device 310 further comprises a table 314 with placed thereon a patient 316. In this example, the medical imaging device 310 is an X-ray imaging device, though devices using other imaging methods may be employed as well.

The medical imaging device 310 may be provided with a data processing system 300 as an example of the second aspect, which may be connected with a link 318 to the imaging unit 312 such that the system 300 may receive frames with image data directly from the imaging unit 312. The data processing system 300 may be further embodied as a dedicated computer, a general purpose computer, other, or a combination thereof. The system 300 will be elaborated on in conjunction with FIG. 1B.

In the second position, the imaging unit 312 has been rotated over an angle α relative to the table 314. The angle α is preferably within a range of 25° and 50° and more preferably within a range between 35° and 40°. This allows the imaging unit 312 to capture a first video stream in the first position comprising first consecutive frames comprising image data on the cardiovascular system of the patient 316 in a first orientation, and to capture a second video stream in the second position comprising second consecutive frames comprising image data on the cardiovascular system of the patient 316 in a second orientation.

Figure 1B:
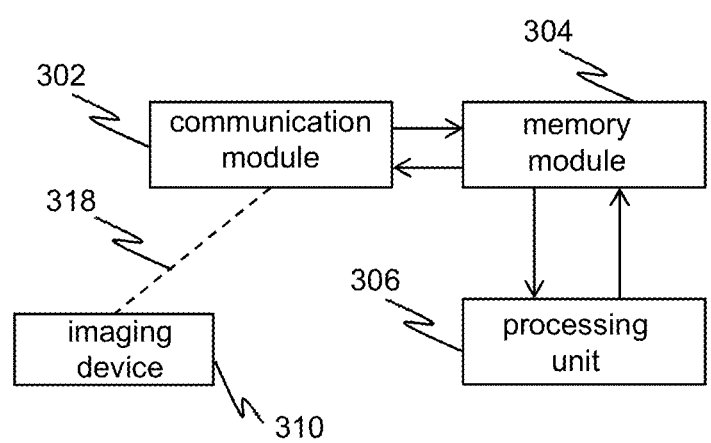
FIG. 1B shows an example of a data processing system.

FIG. 1B shows the data processing system 300 in further detail. The data processing system 300 comprises means for carrying out a method of building a 3D model of at least a part of a cardiovascular system according to any of the examples of this description, based on images acquired by means of the medical imaging device 310.

The system 300 comprises a communication module 302 for receiving the first video stream and the second video stream. The communication module 302 may be directly interconnected with the medical imaging device 310 via link 318. The communication module 302 is in communicative connection with a memory module 304 such that data may be transferred between the communication module 302 and the memory module 304.

The system 300 further comprises a processing unit 306 arranged for performing one or more steps of examples of the method of building a 3D model of at least a part of a cardiovascular system. The processing unit 306 is in communicative connection with the memory module 304 such that the processing unit 306 may at least retrieve data from the memory module 304 and store data on the memory module 304.

The communication module 302 may comprise one or more inputs, such as input ports such as USB ports, Ethernet ports, Bluetooth, any other input, or any combination thereof for receiving data. Connected to an input port of the communication module 302 may be one or more user input devices such as a mouse, keyboard, touchscreen, joystick, any other user input device, or any combination thereof, such that the system 300 may receive data related to a user input.

The communication module 302 may further comprise one or more outputs such as output ports such as USB ports, Ethernet ports, any other output, or any combination thereof for outputting data. Such outputting of data may be to a display device like a screen, a printer, a force feedback device, other, or a combination thereof. A communication port of the communication module 302 may also be simultaneously arranged for receiving data and outputting data.

Data received by the communication module 302 may be in the form of video streams comprising frames comprising image data such as the first video stream and the second video stream. Such video streams may be stored on the memory module 304 such that they may be accessed by the processing unit 306. Video stream data may be received directly from a medical imaging device 310 for example via link 318 and/or via an additional data storage medium, such as a USB stick, hard disk drive, solid state drive, or a remote location on the Internet, an intranet, or any other remote location.

The communication module 302 may further be arranged for receiving cardiac cycle data, for example from an electrocardiography device, a photoplethysmography device, or any other device for obtaining cardiac cycle data. The cardiac cycle data may be stored on the memory module 304 such that it may be accessed by the processing unit 306. Cardiac cycle data may either be received directly from such a device for obtaining cardiac cycle data or via an additional data storage medium, such as a USB stick, hard disk drive, solid state drive, or a remote location on the Internet, an intranet, or any other remote or local location. In the latter case, the cardiac cycle data may be combined with the first video stream and the second video stream, with the cardiac cycle data and the image data being aligned in time.

Data outputted by the communication module 302 may for example be the 3D model of part of the cardiovascular system built using an example the method of building a 3D model of at least a part of a cardiovascular system.

The memory module 304 may comprise a transient memory and/or a non-transient memory, and may comprise one or more of a hard-disk drive, solid state drive, flash memory, RAM memory, any other type of memory or any combination thereof.

Stored on the memory module 304 may be a computer program product comprising instructions which, when the program is executed by the system 300, cause the system 300 to carry out the method of building a 3D model of at least a part of a cardiovascular system according to any of the examples disclosed herein. As such, the memory module 304 may be a computer-readable storage medium comprising instructions which, when executed by the system 300, cause the system 300 to carry out the method of building a 3D model of at least a part of a cardiovascular system according to any of the examples disclosed herein.

The memory module 304 may thus be provided on its own outside the system 300, and may be connected to a generic computer device arranged for communication with the memory module 304 and executing instructions stored on the memory module 304. As such, the memory module 304 may be arranged as a USB stick, compact disc, DVD, flash drive, SD card, or any other memory device.

The processing unit 306 may comprise one or both of a Central Processing Unit (CPU) and a Graphical Processing Unit (GPU) for executing one or more steps of the method 100. The processing unit 306 may further be arranged for retrieving the first video stream and the second video stream from the memory module 304.

When executing some of the examples of the method of building a 3D model of at least a part of a cardiovascular system on the system 300, the cardiac cycle data may be present on the memory module 304 and may thus be retrieved from the memory module 304 by the processing unit 306.

Cardiac cycle data may comprise heart activity data on a particular state of the heart at a particular point in time. For ECG data, it represents neural activity of the heart; for photoplethysmography data it represents blood density in, for example, a tip of a finger or an earlobe. From this heart activity data, a state of the heart or a particular cycle event in a cardiac cycle and timing data related to such an event may be determined. Depending on the method of acquisition and resolution of cardiac cycle data, the start or end of a systolic or diastolic event may be determined, with data on timing of the start or the end thereof. In other examples, a particular point between start and end may be determined.

When executing some other examples of the method of building a 3D model of at least a part of a cardiovascular system on the system 300, the cardiac cycle data may be obtained by the processing unit 306, for example from the first video stream and the second video stream, from electrocardiography data or from photoplethysmography data.

In such examples, the processing unit 306 is arranged to generate cardiac cycle data by for example analysing the first video stream and the second video stream. Such an analysis may comprise detecting points of interest or regions of interest in frames of the video streams, which may correspond to locations of arteries or locations of specific points in the arteries, like branches. When using X-ray, such points may be made visible or more visible by injecting contrast dye in the arteries. By analysing the position of branch points or regions of interest in consecutive frames, movement of the points or regions of interest in time may be detected from which cardiac cycle data may be deducted. To this end, computer vision techniques such as vessel segmentation, centerline detection, object tracking and motion detection, or any combination thereof may be used. Alternatively or additionally, a user may provide one or more points or regions of interest.

When the processing unit 306 is arranged to generate cardiac cycle data from electrocardiographic data or from photoplethysmography data, the processing unit 306 is arranged for analysing these types of data and deducing cardiac cycle data from said types of data. To this end, signal processing techniques such as high-frequency filtering, derivative calculation, QRS-complex detection and adaptive signal thresholding may be applied for the electrocardiographic data.

Techniques such as machine learning or artificial intelligence may be applied by the processing unit 306 to eventually obtain cardiac cycle data from the first period of time and the second period of time to be later-on used for selecting one of the first frames and one of the second frames for building the 3D model of part of the cardiovascular system using the selected frames.

The processing unit 306 may thus be arranged for selecting one of the first frames out of the first video stream and selecting one of the second frames out of the second video stream based on the cardiac cycle data in steps 110 and 112.

The processing unit 306 may be arranged for combining data from the selected one of the first frames and the selected one of the second frames for building the 3D model of part of the cardiovascular system.

Figure 2:
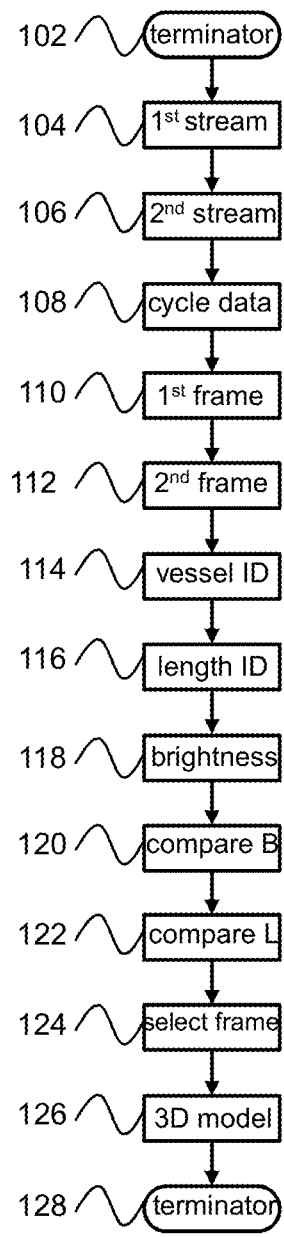
FIG. 2 shows a flowchart of a method of building a 3D model of at least a part of a cardiovascular system.
Figure 3:
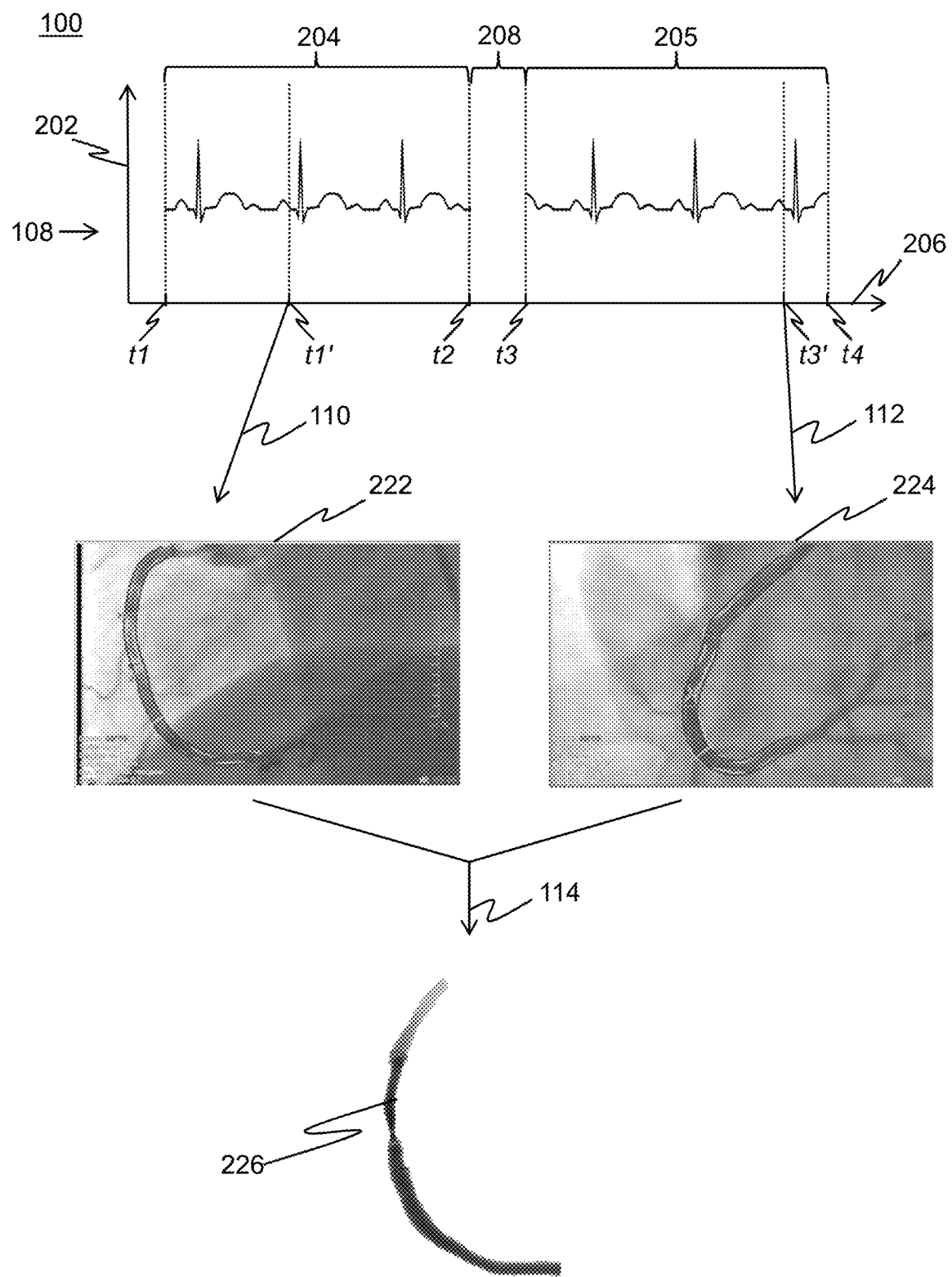
FIG. 3 shows a visualised representation of part of the method.

FIG. 2 shows a flowchart of a method 100 for building a 3D model of at least a part of a cardiovascular system and will be used in conjunction with FIG. 3 to describe examples of the method 100.

The method 100 starts at terminator 102, and continues with receiving a first video stream comprising first frames comprising image data on a cardiovascular system over a first period of time at step 104. Step 104 is followed by receiving a second video stream comprising second frames comprising image data on the cardiovascular system over a second period of time in step 106.

The method 100 further comprises obtaining cardiac cycle data based on data obtained from the patient 316 over the first period of time and the second period of time in step 108. In FIG. 3, an example of cardiac cycle data 202 from the first period of time 204 and the second period of time 205 is shown plotted over a horizontal time axis 206. The first period of time 204 extends between a time t1 and a time t2, as indicated on the time axis 206. The second period of time 205 extends between a time t3 and a time t4, as indicated on the time axis 206.

Between the first period of time 204 and the second period of time 205 a time gap 208 as a reorientation time is present between capturing the first frames of the first video stream during the first period of time 204 and capturing the second frames of the second video stream during the second period of time 205. During the time gap 208, the imaging device 312 may be reoriented relative to the cardiovascular system as shown in FIG. 1A. The time gap may be seconds or minutes—or zero. In yet another example, the first period of time 204 and the second period of time may overlap partially or fully.

Note that the time scale 206 may not be a linear scale as shown in FIG. 3, and that the time gap 208 may comprise more seconds or minutes than the first period of time 204 and/or the second period of time 205.

Further, note that the first period of time 204 and/or the second period of time 205 may comprise a plurality of cardiac cycles, and therefor more than one frame within the first video stream and/or second video stream may correspond to a certain cardiac cycle event. For example, in the first period of time 204 and the second period of time 205 as shown in FIG. 3 comprise approximately three cardiac cycles.

From data acquired from the patient 316, as discussed above, cardiac cycle data may be determined, like the start or end of a systolic or diastolic phase of a heartbeat cycle, at specific points on the timeline, for the first period of time 204 and the second period of time 206.

Referring back to FIG. 2, next, respectively in steps 110 and 112, the method 100 comprises selecting one of the first frames and selecting one of the second frames based on the cardiac cycle data.

As shown in FIG. 3, one of the first frames 222 is selected based on the cardiac cycle data 202, wherein the one of first frames 222 has been captured at a time t1' within the first period of time 204. In step 112, one of the second frames 224 is selected based on the cardiac cycle data 202, wherein the one of second frames 224 has been captured at a time t2' within the second period of time 205. The 3D model 226 is built using the one of first frames 222 and the one of the second frames 224.

The times t1' and t2', and the corresponding frames 222 and 224, have been automatically selected based on the cardiac cycle data 202 according to the first aspect. More in particular, t1' and t2' correspond to the end of the diastolic phase. At the end of the diastolic phase, the heart and the left ventricle in particular is at its largest size. In this state, the arteries are stretched and spaced apart as much as possible. This may enhance visibility of the arteries and minimize any foreshortening.

To provide automated selection of frames from the first video stream and the second video stream, the obtained cardiac cycle data is processed for detecting at which point or points in time the start or end of the systolic or diastolic cycle is, thus yielding cardiac cycle state data. As discussed, preferably a frame or frames close to or at the end of the diastolic phase is selected; these frames are also referred to as ED frames.

The selected frame or frames may be processed further fully automatically. Alternatively, the selected frame or frames are presented to a user on a screen, for confirmation of the selection in case a single frame is provided. In case multiple frames are provided, a user may select one of the frames or confirm use of all frames for setting up a model. In one example, a user may select in one or more frames from each of the video streams points of interest. Such identification aids in forming the model by matching identical points of frames of the first video stream and the second video stream.

In case multiple frames of the vessel under scrutiny at the end of the diastolic phase are selected, it may be preferred to provide automatic selection, from the group of earlier selected frames, of a frame that may be considered as more appropriate for building the three-dimensional model of the vessel under scrutiny. In one embodiment, in subsequent selected frames, the vessel under scrutiny is identified 114. Preferably, also a direction of fluid flow is determined, which allows to optionally determine an upstream end and a downstream end.

With the vessel identified, it is possible to determine a trajectory of the vessel in which the contrast fluid is provided. With this information, it is also possible to determine the length of the vessel—or a least of the trajectory in which contrast fluid is available. On one hand, it is preferred to use a selected end diastolic frame of which the longest vessel length can be used. On the other hand, it may be preferred that the proximal end of the vessel, at which side the catheter is provided for entering the contrast fluid, comprises sufficient contrast fluid for detecting this proximal end of the vessel.

The level of contrast fluid in the vessel may preferably be above a particular level, i.e. where above a particular level of dilution of contrast fluid in blood. In order to facilitate selection an ED frame that may be considered best for building the 3D model, it is preferred to select an ED frame that is best filled with contrast fluid, yet least diluted.

Hence, for automatic selection of a preferred ED frame, the vessel under scrutiny is identified in all ED frames selected in step 110 and step 112. The detection may be executed using any technology, such as image edge detection. Subsequently, the length of the identified vessel is determined in step 116, for example using image processing algorithms, in each ED frame. The length may be determined in pixels, one or more SI units, other, or any combination thereof.

Subsequently or in parallel, brightness of pixels within the region of the identified vessel is assessed 118. Such assessment may take place on a per pixel basis, over the whole region of the identified vessel or in a sub-region of the vessel region larger than a single pixel. In case brightness of a region with multiple pixels is assessed, average or median brightness may be assessed and other statistical parameters may be used, like standard deviation and/or removal of outliers.

As indicated, it may be preferred that in a selected frame, the contrast fluid is available at the upstream end of the vessel, at the outlet of the catheter used for inserting contrast fluid. In such embodiment and possibly also other embodiments, it is preferred to determine a location of the outlet of the catheter. This may be done by selecting any frame, not necessarily an ED frame, at the start of any sequence, prior to injection of the contrast fluid in the vessel. In such frame, the catheter is visible and may be identified.

Next, within the vessel region or vessel sub-regions, brightness levels are compared 120 over subsequent ED frames. In a particular embodiment, brightness levels in sub-regions at, adjacent to or near the identified catheter outlet are compared in subsequent ED frames. Subsequently or concurrently, the lengths of the identified vessels in the ED frames are compared in step 122, preferably for subsequent ED frames.

In step 124, a preferred ED frame is selected for each angle under which the frames have been acquired. In the selection step, results of the comparing of the previous two steps may be taken into account. Various embodiments may use different criteria: the longest identified vessel, the lowest brightness (most radiation blocked by highest concentration of contrast fluid), the lowest brightness at the catheter outlet, other, or a combination thereof.

In a particularly preferred embodiment, the longest identified vessel is selected that has the lowest median or average brightness, either as a whole or in a particular region, like the catheter outlet region. In another preferred embodiment, the longest identified vessel is selected that has a lower average or median brightness than the subsequent ED frame, either over the whole vessel frame region or a vessel sub-region, in particular at or near the outlet end of the catheter.

Finally, the method 100 comprises building the 3D model of part of the cardiovascular system using the selected frames in step 126 and ends in terminator 128. Building of such model of the human cardiovascular system based on two selected x-ray images is known to the skilled person in cardiology.

Further required for building the 3D model may be knowledge on the orientation and/or position of the imaging device 312 relative to the cardiovascular system of the patient during the capturing of the selected one of the first frames and during the capturing of the selected one of the second frames.

The ultimately selected one of the first frames and the selected one of the second frames may be presented to a user prior to building the 3D model for identification of relevant parts of cardiovascular systems in the frames and/or verification.

Note that the different steps of method 100 may be performed in the sequences as described in conjunction with FIG. 2, but may also performed in any other suitable order as will be appreciated by a person skilled in the art.

In summary, to create a 3D model of part of a cardiovascular system, two 2D images taken of different orientations of the cardiovascular system may be combined. The 2D images originate from video streams taken at different points in time, which comprise frames showing a beating heart, and thus a moving cardiovascular system. Because of this movement, not just any random set of two 2D images may result in useable 3D model. To select a proper set of two 2D images, a method is provided wherein said selection is based on cardiac cycle data. The cardiac cycle data may comprise heart activity data as a function of time and timing data on cycle events. These cycle events may be repetitive, as the same events occur with every heartbeat. The selected frames are preferably selected at, or approximately at, similar events.

In the description above, it will be understood that when an element such as layer, region or substrate is referred to as being "on" or "onto" another element, the element is either directly on the other element, or intervening elements may also be present. Also, it will be understood that the values given in the description above, are given by way of example and that other values may be possible and/or may be strived for.

The various aspects may be implemented in hardware, software or a combination thereof. The data to be processed may be digital or analogue or a combination thereof. In case analogue data is provided or received and digital data is required for processing, analogue to digital conversion may be used and subsequently, the digital data is processed.

Furthermore, the invention may also be embodied with less components than provided in the examples described here, wherein one component carries out multiple functions. Just as well may the invention be embodied using more elements than depicted in the Figures, wherein functions carried out by one component in the example provided are distributed over multiple components.

It is to be noted that the figures are only schematic representations of examples of the invention that are given by way of non-limiting examples. For the purpose of clarity and a concise description, features are described herein as part of the same or separate examples, however, it will be appreciated that the scope of the invention may include examples having combinations of all or some of the features described. The word 'comprising' does not exclude the presence of other features or steps than those listed in a claim. Furthermore, the words 'a' and 'an' shall not be construed as limited to 'only one', but instead are used to mean 'at least one', and do not exclude a plurality.

A person skilled in the art will readily appreciate that various parameters and values thereof disclosed in the description may be modified and that various examples disclosed and/or claimed may be combined without departing from the scope of the invention.

It is stipulated that the reference signs in the claims do not limit the scope of the claims, but are merely inserted to enhance the legibility of the claims.

What is claimed is:

1. A method of building a 3D model of at least a part of a cardiovascular system of a person, comprising:
   receiving a first video stream comprising first frames comprising image data on the cardiovascular system over a first period of time;
   receiving a second video stream comprising second frames comprising image data on the cardiovascular system over a second period of time, wherein the first period of time is in disjunction from the second period of time;
   obtaining cardiac cycle data related to the cardiovascular system from the first period of time and the second period of time;
   selecting at least one of the first frames and at least one of the second frames based on the cardiac cycle data; and
   building the 3D model of part of the cardiovascular system using the selected frames,
   wherein the cardiac cycle data comprises timing data on a first cycle event within the first period of time and timing data on a second cycle event within the second period of time, and the selecting of the at least one of the first frames is based on the timing data of the first cycle event and the selecting of the at least one of the second frames is based on the timing data of the second cycle event.

2. The method according to claim 1, wherein the cardiac cycle data comprises heart activity data as a function of time.

3. The method according to claim 1, wherein the second cycle event is equivalent to the first cycle event.

4. The method according to claim 1, further comprising:
   selecting, from the first frames, based on the first cycle event, multiple first selected frames related to the first cycle event;
   selecting, from the second frames, based on the second cycle event, multiple second selected frames related to the second cycle event;
   identifying, in at least a first of the first selected frames and the second selected frames, a first image region depicting a cardiovascular structure;
   comparing, in the first of the first selected frames and the second selected frames, at least one characteristic of the first image region;
   based on the comparing, selecting from the first of the first selected frames and the second selected frames, a first model frame; and
   building the 3D model using the first model frame.

5. The method according to claim 4, further comprising:
   identifying, in a second of the first selected frames and the second selected frames, a second image region depicting the cardiovascular structure;
   comparing, in the second of the first selected frames and the second selected frames, at least one characteristic of the second image region;
   based on the comparing, selecting from the second of the first selected frames and the second selected frames, a second model frame; and
   building the 3D model using the first model frame and the second model frame.

6. The method according to claim 4, further comprising determining, in the first of the first selected frames and the second selected frames, a length of the cardiovascular structure;
   wherein the at least one characteristic of the first image region is the length of the cardiovascular structure.

7. The method according to claim 4, further comprising determining, within the first image region depicting the cardiovascular structure, in at least the first of the first selected frames and the second selected frames, a brightness level of the first image region or a sub-region thereof;
wherein the at least one characteristic of the first image region is the brightness level.

8. The method according to claim 4, wherein, in the step of comparing, the first of the first selected frames and the second selected frames are subsequent in time.

9. The method according to claim 8, further comprising determining, within the first image region depicting the cardiovascular structure, in the first of the first selected frames and the second selected frames, a brightness level of the first image region or a sub-region thereof;
wherein:
the at least one characteristic of the first image region is the brightness level; and
the first model frame is selected based on having the brightness level that is lower than that of the first image region or sub-region thereof in a subsequent frame.

10. The method according to claim 8, further comprising:
determining, in the first of the first selected frames and the second selected frames, a length of the cardiovascular structure; and
determining, within the first image region depicting the cardiovascular structure, in the first of the first selected frames and the second selected frames, a brightness level of the first image region or a sub-region thereof;
wherein:
one of the at least one characteristic of the first image region is the length of the cardiovascular structure; and
another of the at least one characteristic of the first image region is the brightness level; and
the first model frame is selected based on having the longest length and the brightness level that is lower than that of the first image region or sub-region thereof in a subsequent frame.

11. The method according to claim 1, wherein the first cycle event and the second cycle event correspond to an end of diastole.

12. The method according to claim 1, further comprising receiving electrocardiography data from the first period of time and the second period of time, wherein the cardiac cycle data is obtained from the electrocardiography data.

13. The method according to claim 1, further comprising receiving photoplethysmography data from the first period of time and the second period of time, wherein the cardiac cycle data is obtained from the photoplethysmography data.

14. The method according to claim 1, wherein the image data over the first period of time and the second period of time are obtained by a single medical imaging device.

15. The method according to claim 1, carried out by a computer.

16. A non-transitory computer-readable storage medium comprising instructions which, when executed by a computer, cause the computer to carry out the method of claim 1.

17. A method of building a 3D model of at least a part of a cardiovascular system of a person, comprising:
receiving a first video stream comprising first frames comprising image data on the cardiovascular system over a first period of time;
receiving a second video stream comprising second frames comprising image data on the cardiovascular system over a second period of time, wherein the first period of time and the second period of time partially or fully overlap;
obtaining cardiac cycle data related to the cardiovascular system from the first period of time and the second period of time;
selecting at least one of the first frames and at least one of the second frames based on the cardiac cycle data; and
building the 3D model of part of the cardiovascular system using the selected frames,
wherein the cardiac cycle data comprises timing data on a first cycle event within the first period of time and timing data on a second cycle event within the second period of time, and the selecting of the at least one of the first frames is based on the timing data of the first cycle event and the selecting of the at least one of the second frames is based on the timing data of the second cycle event.

18. The method according to claim 17, wherein the cardiac cycle data comprises heart activity data as a function of time.

19. The method according to claim 17, wherein the second cycle event is equivalent to the first cycle event.

20. The method according to claim 17, further comprising:
selecting, from the first frames, based on the first cycle event, multiple first selected frames related to the first cycle event;
selecting, from the second frames, based on the second cycle event, multiple second selected frames related to the second cycle event;
identifying, in at least a first of the first selected frames and the second selected frames, a first image region depicting a cardiovascular structure;
comparing, in the first of the first selected frames and the second selected frames, at least one characteristic of the first image region;
based on the comparing, selecting from the first of the first selected frames and the second selected frames, a first model frame; and
building the 3D model using the first model frame.

* * * * *